(12) United States Patent
Fell et al.

(10) Patent No.: US 7,514,562 B2
(45) Date of Patent: Apr. 7, 2009

(54) UREA DERIVATIVES AND THEIR USE AS VANILLOID RECEPTOR ANTAGONISTS IN THE TREATMENT OF PAIN

(75) Inventors: Stephen Christopher Martin Fell, Harlow (GB); Harshad Kantilal Rami, Harlow (GB); Mervyn Thompson, Harlow (GB); David Richard Witty, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 581 days.

(21) Appl. No.: 10/548,132

(22) PCT Filed: Mar. 4, 2004

(86) PCT No.: PCT/EP2004/002377

§ 371 (c)(1),
(2), (4) Date: Sep. 6, 2005

(87) PCT Pub. No.: WO2004/078744

PCT Pub. Date: Sep. 16, 2004

(65) Prior Publication Data

US 2006/0276447 A1    Dec. 7, 2006

(30) Foreign Application Priority Data

Mar. 7, 2003  (GB) ................... 0305290.9
Mar. 7, 2003  (GB) ................... 0305291.7

(51) Int. Cl.
*C07D 401/02*   (2006.01)
*A61K 31/435*   (2006.01)

(52) U.S. Cl. .................. 546/276.4; 514/210.2

(58) Field of Classification Search ............. 546/276.4; 514/210.2
See application file for complete search history.

(56) References Cited

U.S. PATENT DOCUMENTS

| | | | | |
|---|---|---|---|---|
| 3,424,760 | A * | 1/1969 | Welstead, Jr. et al. ....... | 548/557 |
| 5,621,010 | A * | 4/1997 | Sueda et al. ................. | 514/596 |
| 5,925,635 | A | 7/1999 | Maduskuie, Jr. et al. | |
| 6,355,631 | B1 | 3/2002 | Achard et al. | |
| 6,506,572 | B2 | 1/2003 | Biedermann et al. | |
| 6,602,882 | B1 | 8/2003 | Davies et al. | |
| 6,723,730 | B2 | 4/2004 | Bakthavatchalam et al. | |
| 6,903,085 | B1 | 6/2005 | Thom et al. | |
| 2003/0153568 | A1 | 8/2003 | Cusack et al. | |
| 2004/0082661 | A1 | 4/2004 | Rami et al. | |
| 2004/0171639 | A1 | 9/2004 | Rami et al. | |
| 2005/0113414 | A1 | 5/2005 | Watson et al. | |
| 2006/0094716 | A1 * | 5/2006 | Aissaoui et al. .......... | 514/232.5 |

FOREIGN PATENT DOCUMENTS

| | | |
|---|---|---|
| DE | 28 16 884 | 11/1978 |
| DE | 199 55 794 | 5/2000 |
| EP | 0416581 | 3/1991 |
| EP | 0591030 | 4/1994 |
| EP | 0625507 | 11/1994 |
| EP | 0628310 | 12/1994 |
| ES | 2007808 | 7/1989 |
| WO | WO 00/50399 * | 8/2000 |
| WO | WO00/71171 | 11/2000 |
| WO | WO01/07409 | 2/2001 |
| WO | WO03/022809 | 3/2003 |
| WO | WO03/072545 | 9/2003 |
| WO | WO2004/024710 | 3/2004 |
| WO | WO2004/026836 | 4/2004 |
| WO | WO2004/078101 | 9/2004 |
| WO | WO2004/078749 | 9/2004 |

OTHER PUBLICATIONS

Frigola et al., *Journal of Medicinal Chemistry* vol. 36 No. 7 1993 pp. 801-810.
Carling et al., *Journal of Medicinal Chemistry* vol. 42 No. 14 (1999) pp. 2706-2715.
Huang et al., *Journal of Medicinal Chemistry* vol. 41 No. 13 (1998) pp. 2361-2370.
Huang et al., *Journal of Medicinal Chemistry* vol. 44 No. 25 (2001) pp. 4404-4415.

* cited by examiner

*Primary Examiner*—Rita J Desai
*Assistant Examiner*—John Mabry
(74) *Attorney, Agent, or Firm*—Reid S. Willis; Charles M. Kinzig

(57) ABSTRACT

Compounds of formula (I),

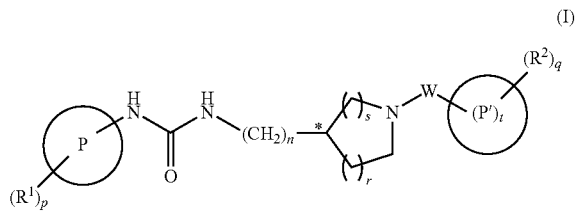

or a pharmaceutically acceptable salt or solvate thereof, wherein P, P', W, $R^1$, $R^2$, n, p, q, r, s and t are as defined in the specification, processes for preparing such compounds, pharmaceutical compositions comprising such compounds and their use in therapy.

14 Claims, No Drawings

UREA DERIVATIVES AND THEIR USE AS VANILLOID RECEPTOR ANTAGONISTS IN THE TREATMENT OF PAIN

This invention relates to novel compounds, especially urea derivatives, having pharmacological activity, processes for their preparation, to compositions containing them and to their use in medicine, especially in the treatment of various disorders.

Vanilloids are a class of natural and synthetic compounds that are characterised by the presence of a vanillyl (4-hydroxy 3-methoxybenzyl) group or a functionally equivalent group. Vanilloid Receptor (VR1), whose function is modulated by such compounds, has been widely studied and is extensively reviewed by Szallasi and Blumberg (The American Society for Pharmacology and Experimental Therapeutics, 1999, Vol. 51, No. 2.).

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant capsazepine (*Tetrahedron,* 53, 1997, 4791) and olvanil or —N-(4-hydroxy-3-methoxybenzyl)oleamide (*J. Med. Chem.,* 36, 1993, 2595).

U.S. Pat. No. 3,424,760 and U.S. Pat. No. 3,424,761 both describe a series of 3-ureidopyrrolidines that are said to exhibit analgesic, central nervous system, and psychopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively.

International Patent Application, Publication Number WO 97/43255, discloses azetidinylurea derivatives as inhibitors of microsomal triglyceride transfer protein.

International Patent Applications, Publication Numbers WO 02/08221, WO 02/16317, WO 02/16318 and WO 02/16319 each disclose certain vanilloid receptor antagonists and their use in the treatment of diseases associated with VR1 activity.

International Patent Applications, Publication Numbers WO 02/072536 and WO 02/090326, and International Patent Application, Publication Number WO 03/022809 (published after the priority date of the present application) disclose a series of urea derivatives and their use in the treatment of diseases associated with VR1 activity. None of these applications discloses azetidinylurea derivatives in particular azetidin-3-ylurea derivatives.

According to a first aspect of the present invention, there is provided a compound of formula (I),

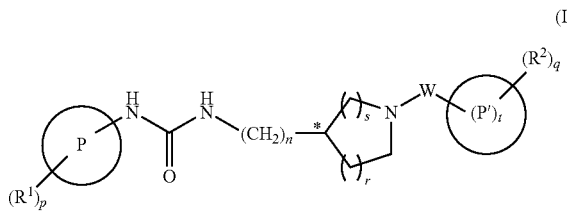

(I)

or a pharmaceutically acceptable salt thereof, or a solvate thereof, wherein:

P and P' are independently selected from aryl and heteroaryl;
$R^1$ and $R^2$ are independently selected from —H, halo, alkyl, alkoxy, cycloalkyl, aralkyl, aralkoxy, cycloalkylalkyl, cycloalkylalkoxy, —CN, —NO$_2$, —OH, —OCF$_3$, —CF$_3$, —NR$^4$R$^5$, —S(O)$_m$R$^6$, —S(O)$_2$NR$^4$R$^5$, —OS(O)$_2$R$^6$, —OS(O)$_2$CF$_3$, —O(CH$_2$)$_x$NR$^4$R$^5$, —C(O)CF$_3$, —C(O)alkyl, —C(O)cycloalkyl, —C(O)aralkyl, —C(O)Ar, —C(O)(CH$_2$)$_x$OR$^6$, —C(O)(CH$_2$)$_x$NR$^4$R$^5$, —C(O)alkoxy, —C(O)NR$^4$R$^5$, —(CH$_2$)$_x$C(O)alkoxy, —(CH$_2$)$_x$OC(O)R$^6$, —(CH$_2$)$_x$OR$^6$, —(CH$_2$)$_x$NR$^4$R$^5$, —(CH$_2$)$_x$C(O)NR$^4$R$^5$, —(CH$_2$)$_x$N(R$^4$)C(O)R$^6$, —(CH$_2$)$_x$S(O)$_2$NR$^4$R$^5$, —(CH$_2$)$_x$N(R$^4$)S(O)$_2$R$^6$, -ZAr, —(CH$_2$)$_x$S(O)$_2$R$^6$, —(OCH$_2$)$_x$S(O)$_2$R$^6$, —N(R$^4$)S(O)$_2$R$^6$, —N(R$^4$)C(O)R$^6$ or —(CH$_2$)$_x$C(O)alkyl;
$R^4$ and $R^5$ may be the same or different and represent H or alkyl or $R^4$ and $R^5$ together with the atoms to which they are attached form a $C_{3-6}$azacycloalkane, $C_{3-6}$(2-oxo)azacycloalkane ring or $C_{5-8}$ polymethylene chain optionally interrupted by heteroatoms;
Z represents O, S or NR$^7$;
W represents a bond or a group CH or (CH$_2$)CH;
$R^6$ represents alkyl or aryl;
$R^7$ represents hydrogen, alkyl or aryl;
m represents and integer 1 or 2;
n represents and integer 0, 1, 2 or 3;
p and q independently represent an integer 0, 1, 2, 3 or 4;
when W is a bond, t represents 1, r represents an integer 0 or 1, and s represents an integer 0 or 1, such that r+s=1;
when W is a group CH or (CH$_2$)CH, t represents 2, r represents an integer 0, 1, 2 or 3, and s represents an integer 0, 1 or 2; and
x represents an integer 0, 1, 2, 3, 4, 5 or 6.

Examples of the $C_{3-6}$azacycloalkane ring that $R^4$ and $R^5$ may independently represent, when taken together with the atoms to which they are attached, include pyrrolidine and piperidine.

Examples of the $C_{3-6}$(2-oxo)azacycloalkane ring that $R^4$ and $R^5$ may independently represent, when taken together with the atoms to which they are attached, include pyrrolidinone and piperidinone.

Examples of the $C_{5-8}$ polymethylene chain optionally interrupted by heteroatoms that $R^4$ and $R^5$ may independently represent when taken together with the atoms to which they are attached, include a $C_{5-8}$ polymethylene chain optionally interrupted by heteroatoms such as 0 or —NR$^7$. Specific examples include morpholine and piperazine.

When p or q represent 2, 3 or 4 the groups $R^1$ or $R^2$ may be the same or different.

Preferably, P represents phenyl, naphthyl, quinolinyl, cinnolinyl or isoquinolinyl, more preferably phenyl, cinnolinyl or isoquinolinyl, particularly phenyl, 5-cinnolinyl or 5-isoquinolinyl. More preferably, when W is a bond, P represents phenyl or 5-isoquinolinyl, especially phenyl, and, when W is CH or (CH$_2$)CH, P represents 5-cinnolinyl or 5-isoquinolinyl, especially 5-isoquinolinyl. When W is CH or (CH$_2$)CH, another P group of interest is phenyl.

Preferably, P' represents a 6-membered aromatic ring e.g. phenyl, pyrimidinyl or pyridyl, especially phenyl or pyridyl e.g. 2-pyridyl. More preferably, when W is a bond, P' represents phenyl or pyridyl, especially 2-pyridyl, and, when W is CH or (CH$_2$)CH, P' represents phenyl.

Preferably, $R^1$ represents halo, —CF$_3$ or alkyl. More preferably, $R^1$ represents fluoro, chloro, bromo, —CF$_3$, methyl or tert-butyl, especially fluoro, chloro, bromo, —CF$_3$ or methyl, more especially fluoro, chloro, bromo or methyl In particular, when W is a group CH or (CH$_2$)CH, $R^1$ preferably represents methyl. When W is a group CH or (CH$_2$)CH, another $R^1$ substituent of interest is bromo. When W is a bond, $R^1$ preferably represents chloro or bromo.

Preferably, p represents 1 or 2. More preferably, p represents 1.

Particular groups which $(R^1)_pP-$ may represent include, 2-, 3- or 4-halophenyl or 2,3- or 2,5-dihalophenyl e.g. 2-bromophenyl, 2-chlorophenyl, 3-chlorophenyl, 4-fluorophenyl, 2,3-dichlorophenyl or 2,5-dichlorophenyl, 2- or 3-trifluoromethylphenyl, 2-methyl-3-chlorophenyl, 1- or 3-methylisoquinolin-5-yl, 1,3-dimethylisoquinolin-5-yl or 3-methylcinnolin-5-yl.

Preferably, m represents 1.

Preferably, n represents 0 or 1. More preferably, n represents 0.

Preferably, $R^2$ represents halo, alkyl, alkoxy, —CN or —$CF_3$. More preferably $R^2$ represents fluoro, chloro, bromo, methyl, OMe or $CF_3$. In particular, when W is a bond $R^2$ preferably represents methyl or —$CF_3$, especially —$CF_3$, and, when W is CH or $(CH_2)$CH, $R^2$ preferably represents hydrogen or fluoro especially hydrogen.

Preferably, q represents 0, 1 or 2. More preferably, q represents 1 or 2, especially q represents 1. However in one set of compounds of particular interest (notably when W is CH or $(CH_2)$CH and P' represents phenyl) q represents 0.

Preferably, x represents 1, 2 or 3.

When q represents 1 or 2, and P' represents a 6-membered aromatic ring such as phenyl or pyridyl (e.g. 2-pyridyl), particularly preferred examples of $R^2$ are when W is a bond, 3-trifluoromethyl, 4-trifluoromethyl, 5-trifluoromethyl, 6-trifluoromethyl, 6-methyl-4-trifluoromethyl and 6-methyl-5-trifluoromethyl; and when W is CH or $(CH_2)$CH, hydrogen and halo (preferably 4-fluoro).

When W is CH or $(CH_2)$CH, preferably, r+s represents 1, 2, 3 or 4, more preferably 1 or 2, especially 1.

It is especially preferred that r=0 and s=1.

A first group of compounds of particular interest is that in which W represents a bond. A second group of compounds of particular interest is that in which W represents CH or $(CH_2)$CH, particularly CH.

Preferably W represents a bond or CH, most preferably a bond.

Preferably $R^4$ represents methyl or hydrogen

Preferably $R^5$ represents methyl or hydrogen.

Preferably $R^6$ represents methyl.

Preferably $R^7$ represents methyl or hydrogen.

Preferably Z represents a bond.

A particularly preferred group of compounds is that in which r=0, s=1 and P' represents phenyl or 2-pyridyl. In particular, compounds of interest are those in which r=0, s=1, W represents CH or $(CH_2)$CH (especially CH) and P' represents phenyl. Also those in which r=0, s=1, W represents a bond and P' represents 2-pyridyl.

When t is 1, r=1, s=0 and P' is phenyl, P is preferably not phenyl or naphthyl.

While the preferred groups for each variable have generally been listed above separately for each variable, preferred compounds of this invention include those in which several or each variable in formula (I) is selected from the preferred, more preferred, or most preferred groups for each variable. Therefore, this invention is intended to include all combinations of preferred, more preferred, and most preferred groups.

Compounds of formula (I) of particular interest according to the present invention are Example numbers 1 to 41 (presented below) or pharmaceutically acceptable salts or solvates thereof.

Certain of the carbon atoms of formula (I) are chiral carbon atoms, such as the carbon atom marked with an "*", and therefore compounds of formula (I) may exist as stereoisomers. The invention extends to all optical isomers such as stereoisomeric forms of the compounds of formula (I) including enantiomers and mixtures thereof, such as racemates. The different stereoisomeric forms may be separated or resolved one from the other by conventional methods or any given isomer may be obtained by conventional stereospecific or asymmetric syntheses.

An example set of compounds of formula (I) have the C* carbon in the R-configuration.

Certain of the compounds herein can exist in various tautomeric forms and it is to be understood that the invention encompasses all such tautomeric forms.

As indicated above, the compounds of formula (I) can form salts, especially pharmaceutically acceptable salts. Suitable pharmaceutically acceptable salts are those use conventionally in the art and include those described in *J. Pharm. Sci.*, 1977, 66, 1-19, such as acid addition salts.

Suitable pharmaceutically acceptable salts include acid addition salts.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid, glycerophosphoric acid or acetylsalicylic acid.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

The compounds of formula (I) may be prepared in crystalline or non-crystalline form, and if crystalline, may be optionally hydrated or solvated. This invention includes in its scope stoichiometric hydrates as well as compounds containing variable amounts of water.

Suitable solvates include pharmaceutically acceptable solvates, such as hydrates.

Solvates include stoichiometric solvates and non-stoichiometric solvates.

As used herein the term "alkyl" as a group or part of a group refers to a straight or branched chain saturated aliphatic hydrocarbon radical containing 1 to 12 carbon atoms, suitably 1 to 6 carbon atoms. Such alkyl groups in particular include methyl ("Me"), ethyl ("Et"), n-propyl ("Pr$^n$"), iso-propyl ("Pr$^i$"), n-butyl ("Bu$^n$"), sec-butyl ("Bu$^s$"), tert-butyl ("Bu$^t$"), pentyl and hexyl. The term "cycloalkyl" as part of a group refers to a saturated alicyclic hydrocarbon radical containing 3 to 12 carbon atoms, suitably 3 to 6 carbon atoms. Where appropriate, such alkyl groups may be substituted by one or more groups selected from halo (such as fluoro, chloro, bromo), —CN, —$CF_3$, —OH, —$OCF_3$, $C_{2-6}$ alkenyl, $C_{3-6}$ alkynyl, $C_{1-6}$ alkoxy, aryl and di-$C_{1-6}$ alkylamino. Preferably alkyl is unsubstituted.

As used herein, the term "alkoxy" as a group or part of a group refers to an alkyl ether radical, wherein the term "alkyl" is defined above. Such alkoxy groups in particular include methoxy, ethoxy, n-propoxy, iso-propoxy, n-butoxy, iso-butoxy, sec-butoxy and tert-butoxy. Where appropriate, such alkoxy groups may be substituted by one or more groups selected from halo (such as fluoro, chloro, bromo), —CN, —$CF_3$, —OH, —$OCF_3$, $C_{1-6}$ alkyl, $C_{2-6}$ alkenyl, $C_{3-6}$ alkynyl, aryl and di-$C_{1-6}$ alkylamino. Preferably alkoxy is unsubstituted.

As used herein, the term "aryl" as a group or part of a group refers to a carbocyclic aromatic radical ("Ar"). Suitably such aryl groups are 6 membered monocyclic groups or 8-10 membered fused bicyclic groups (including aromatic ring systems fused with non-aromatic ring systems), especially phenyl ("Ph"), biphenyl, indene and naphthyl, particularly phenyl.

Aryl groups contained within moieties $R^1$, $R^2$, $R^6$ or $R^7$ may optionally be substituted (and in the case of bicyclic groups containing an aromatic system fused with a non-aromatic systems may optionally be substituted on either or both of the aromatic and the non-aromatic portion) with one or more substituents selected from the list consisting of halo, hydroxy, carbonyl, alkoxy, alkyl, —$CF_3$, $NR^4R^5$ and —$SO_2R^6$.

As used herein, the term "heteroaryl" as a group or part of a group refers to a stable 5- 7-membered monocyclic or 7- to 10-membered bicyclic heterocyclic aromatic ring (including an aromatic ring system fused with a non-aromatic ring system) which consists of carbon atoms and from 1 to 4 heteroatoms independently selected from the group consisting of N, O and S. It is preferred that the total number of S and O atoms in the aromatic heterocycle is not more than 1. Examples of suitable heteroaryl groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolyl, carbazolyl, carbolinyl, chromanyl, chromenyl, cinnolinyl, decahydroquinolinyl, 2H, 6H-1,5,2-dithiazinyl, dihydrobenzofuranyl, furanyl, furazanyl, imidazolyl, 1H-indazolyl, indolinyl, indolyl, isobenzofuranyl, isochromanyl, isoindazolyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, pyrimidinyl, phthalazinyl, pteridinyl, purinyl, pyrazinyl, pyrazolyl, pyridooxazolyl, pyridoimidazolyl, pyridothiazolyl, pyridyl, pyrrolyl, quinazolinyl, quinolinyl, quinoxalinyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, triazinyl, 1,2,3-triazolyl, 1,2,4-triazolyl, 1,2,5-triazolyl, 1,3,4-triazolyl and xanthenyl.

The term "halo" is used herein to describe, unless otherwise stated, a group selected from fluorine ("fluoro"), chlorine ("chloro"), bromine ("bromo") or iodine ("iodo").

The term "naphthyl" is used herein to denote, unless otherwise stated, both naphth-1-yl and naphth-2-yl groups.

The term "pyridyl" includes 2-pyridyl, 3-pyridyl and 4-pyridyl but preferably denotes 2-pyridyl. The term pyrimidinyl includes 2-pyrimidinyl.

The present invention also provides a process for the preparation of a compound of formula (I) or a pharmaceutically acceptable salt thereof, which process comprises coupling a compound of formula (II):

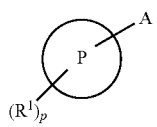

(II)

in which $R^1$, P and p are as defined in formula (I) with a compound of formula (III):

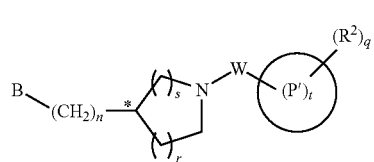

(III)

in which P', $R^2$, W, n, q, r, s and t are as defined in formula (I) and A and B contain appropriate functional groups which are capable of reacting together to form the urea moiety;

and thereafter, as necessary, carrying out one or more of the following reactions:

(i) converting one compound of formula (I) into another compound of formula (I);

(ii) removing any protecting group;

(iii) preparing a salt or a solvate of the compound so formed.

Suitable examples of appropriate A and B groups include:

(a) A is —N═C═O and B is $NH_2$; or A is $NH_2$ and B is N═C═O or (b) A is $NH_2$ and B is $NH_2$ together with an appropriate urea forming agent.

In process (a) the reaction is typically carried out in an inert solvent such as dichloromethane or acetonitrile.

In process (b) the urea forming agent can be carbonyl diimidazole or phosgene or triphosgene, and carried out in an inert organic solvent such as diethyl ether, tetrahydrofuran or DCM at ambient or elevated temperature in the presence of a base such as triethylamine or pyridine.

An alternative method of synthesis of the unsymmetrical urea compounds of formula (I) is from a diaryl carbonate, via the corresponding carbamate. Such a methodology is described by Freer et al. (Synthetic Communications, 26(2), 331-349, 1996). It would be appreciated by those skilled in the art that such a methodology could be readily adapted for preparation of the compounds of formula (I).

A compound of formula (III) may be prepared by reaction of a compound of formula (IV):

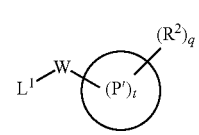

(IV)

wherein, P', W, t, q and $R^2$ as defined above and $L^1$ is a leaving group, with a compound of formula (V):

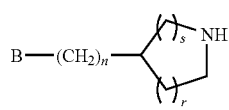

(V)

wherein B, n, r and s are as defined above, or a protected derivative thereof. When B represents an amine group, preferably it is employed as a protected derivative; examples of amine protecting groups are mentioned below.

Suitably $L^1$ is a halogen, such as chlorine.

Suitably, the compound of formula (V) is in an activated form, for example an ionic form. Such activated forms are prepared using conventional coupling reaction methodology, as for example by reacting compounds (IV) and (V) in the presence of an alkali carbonate, such as potassium carbonate, in an aprotic solvent such as dimethylformamide using reaction conditions appropriate to the particular methodology chosen, for example at an elevated temperature, such as 100° C.

Compounds of formulae (IV) and (V) are commercially available, or are prepared by known procedures, such as those disclosed in: *Heterocycles,* 1984, 22(1), 117, J. Chem. Soc., Perkin 1, 1988, 4, 921 and J. Org. Chem., 1991, 56, 6729 for compounds of formula (IV) and *J. Med. Chem.,* 1992, 35(10), 1764 for compounds of formula (V), or by methods analogous to these disclosed methods.

Compounds of formula (II) are either known or may be prepared by known methods, or methods analogous to those described herein.

It will be appreciated by those skilled in the art that it may be necessary to protect certain reactive substituents during some of the above-mentioned procedures. Standard protection and deprotection techniques, such as those described in Greene T. W. 'Protective groups in organic synthesis', New York, Wiley (1981), can be used. For example, primary amines can be protected as phthalimide, benzyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art.

In particular in the reaction of compounds of formula (IV) and (V) the group B preferably represents —NH(t-BOC)—.

Pharmaceutically acceptable salts may be prepared conventionally by reaction with the appropriate acid or acid derivative.

Any novel intermediates used in the synthesis of the compounds of formula (I) are also included within the scope of the invention. Therefore according to the invention there is provided a compound of formula (IIIA):

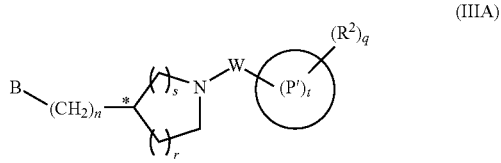

in which P', $R^2$, W, n, q, r, s and t are as defined in formula (I) and B is $NH_2$ or N=C=O.

The preferences for the groups P', $R^2$, W, n, q, r, s and t in formula (IIIA) are the same as those described for formula (I) above.

Specific compounds of formula (IIIA) include:
1-(5-Trifluoromethylpyridin-2-yl)azetidin-3-ylamine;
1-(3-Trifluoromethylpyridin-2-yl)azetidin-3-ylamine;
1-(4-Trifluoromethylpyridin-2-yl)azetidin-3-ylamine;
1-(6-Trifluoromethylpyridin-2-yl)azetidin-3-ylamine;
1-(6-Methyl-4-trifluoromethylpyridin-2-yl)azetidin-3-ylamine;
1-(6-Methyl-5-trifluoromethylpyridin-2-yl)azetidin-3-ylamine;
3-Amino-1-diphenylmethylazetidine; and
3-Amino-1-di-(4-fluorophenyl)methylazetidine.

Compounds of formula (I) and their pharmaceutically acceptable salts have Vanilloid receptor antagonist (VR1) activity and are believed to be of potential use for the treatment or prophylaxis of certain disorders, or treatment of the pain associated with them, such as: pain, chronic pain, neuropathic pain, postoperative pain, postrheumatoid arthritic pain, osteoarthritic pain, back pain, visceral pain, cancer pain, algesia, neuralgia, dental pain, headache, migraine, neuropathies, carpal tunnel syndrome, diabetic neuropathy, HIV-related neuropathy, post-herpetic neuralgia, fibromyalgia, neuritis, sciatica, nerve injury, ischaemia, neurodegeneration, stroke, post stroke pain, multiple sclerosis, respiratory diseases, asthma, cough, COPD, broncho constriction, inflammatory disorders, oesophagitis, heart burn, Barrett's metaplasia, dysphagia, gastroeosophageal relux disorder (GERD), stomach and duodenal ulcers, functional dyspepsia, irritable bowel syndrome, inflammatory bowel disease, colitis, Crohn's disease, pelvic hypersensitivity, pelvic pain, menstrual pain, renal colic, urinary incontinence, cystitis, burns, itch, psoriasis, pruritis, emesis (hereinafter referred to as the "Disorders of the Invention").

Accordingly, the invention also provides a compound of formula (I) or a pharmaceutically acceptable salt or solvate thereof, for use as an active therapeutic substance, in particular in the treatment and/or prophylaxis of the Disorders of the Invention.

In particular, the invention provides a compound of formula (I) or a pharmaceutically acceptable salt or solvate thereof for use in the treatment or prophylaxis of pain.

The invention further provides a method for the treatment or prophylaxis of disorders in which antagonism of the Vanilloid (VR1) receptor is beneficial, in particular the Disorders of the Invention, in mammals including humans, which comprises administering to a mammal in need thereof a therapeutically effective amount of a compound of formula (I) or a pharmaceutically acceptable salt or solvate thereof.

The invention provides for the use of a compound of formula (I) or a pharmaceutically acceptable salt or solvate thereof in the manufacture of a medicament for the treatment or prophylaxis of disorders in which an antagonist of the Vanilloid (VR1) receptor is beneficial, particularly the Disorders of the Invention.

In order to use the compounds of the invention in therapy, they will normally be formulated into a pharmaceutical composition in accordance with standard pharmaceutical practice. Thus, the present invention also provides a pharmaceutical composition, which comprises a compound of formula (I) or a pharmaceutically acceptable salt or solvate thereof and a pharmaceutically acceptable carrier or excipient therefor.

A pharmaceutical composition of the invention, which may be prepared by admixture, suitably at ambient temperature and atmospheric pressure, is usually adapted for oral, parenteral, rectal administration or intravesical adminstration to the bladder and, as such, may be in the form of tablets, capsules, oral liquid preparations, powders, granules, lozenges, reconstitutable powders, injectable or infusable solutions, suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. For systemic administration, dosage levels from 0.01 mg to 100 mg per kilogramme of body weight are useful in the treatment of pain. However, as a general guide suitable unit doses may be 0.05 to 1000 mg, more suitably 0.05 to 20, 20 to 250, or 0.1 to 500.0 mg, for example 0.2 to 5 and 0.1 to 250 mg; and such unit doses may be administered more than once a day, for example two or three a day, so that the total daily dosage is in the range of about 0.5 to 1000 mg; and such therapy may extend for a number of weeks or months.

No unacceptable toxicological effects are indicated with compounds of the invention when administered in accordance with the invention.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of the compounds of the invention.

Abbreviations

BINAP—2,2'-bis(diphenylphosphino)-1,1'-binaphthyl
HPLC—High Perfomance Liquid Chromatography
$MgSO_4$—Magnesium sulfate
TFA—Trifluoroacetic acid
DCM—dichloromethane Description 1

1,3-Dimethyl-5-nitroisoquinoline (D1)

1,3-Dimethylisoquinoline [(*Chem. Left.*, 1983, p. 791), 2.39 g, 15.20 mM], in concentrated sulfuric acid, (15 ml), was cooled to <4° C. A solution of potassium nitrate, (1.69 g, 16.72 mM), in concentrated sulfuric acid was added dropwise, maintaining the temperature below 4° C. After complete addition the solution was stirred at this temperature for a further 2 h then warmed to room temperature for 1 h. The reaction mixture was poured into ice water and the solution basified with sodium hydroxide and extracted with DCM. The extract was washed with brine, dried and concentrated to a yellow solid. Purification by silica gel chromatography afforded the title compound as a yellow crystalline solid.

Description 2

5-Amino-1,3-dimethylisoquinoline (D2)

A solution of D1 (2.01 g, 9.94 mM) and 10% palladium on charcoal (1 g) in methanol was hydrogenated at atmospheric pressure for 1 h. The catalyst was filtered off and the filtrate concentrated under reduced pressure to afford the title compound as an off white solid.

Description 3

3-Methyl-5-nitroisoquinoline (D3)

A solution of 3-methylisoquinoline (5.4 g, 0.038 mol) in concentrated sulfuric acid (30 ml) was cautiously added to a solution of potassium nitrate (4.25 g, 1.1 eq) in concentrated sulfuric acid (23 ml) whilst maintaining the temperature below 4° C. (ice bath). Stirring was continued for 2 h and then temperature raised to ambient. Reaction was further stirred for 3 h and then poured into ice-water slurry (500 ml). Neutralisation using solid potassium carbonate affored a yellow solid which was filtered and washed with water. The crude product was dissolved in ethanol (200 ml), filtered and concentrated under reduced pressure to afford the title compound as a yellow solid.

Description 4

5-Amino-3-methylisoquinoline (D4)

The title compound was prepared from D3 using the procedure outlined in D2.

Description 5

5-Amino-1-methylisoquinoline (D5)

The title compound was prepared in a similar manner to that of K. C. Agrawal, B. A. Booth, A. C. Sartorelli, *J. Med. Chem.*, 1968 11 700.

5-Amino-3-methylcinnoline is available commercially. Di-tert-butyl tricarbonate was prepared according to the procedure outlined in the literature (Org. Synth., 1978, 57, p. 45).

Description 6

[1-(5-Trifluoromethylpyridin-2-yl)azetidin-3-yl]carbamic acid t-butyl ester. (D6)

3-Butoxycarbonylaminoazetidine, acetic acid salt (synthesis described in WO 98/57640) (1 g, 4.31 mM) in dry DMF (10 ml) was treated with 2-chloro-5-trifluoromethylpyridine (938 mg, 5.17 mM) and potassium carbonate (1.43 g, 10.33 mM). The mixture was heated to 100° C. overnight. The solution was diluted with ethyl acetate, washed with water (3×), brine, dried ($MgSO_4$) and concentrated. Purification by silica gel chromatography gave the title compound as a colourless solid, (750 mg).

Description 7

1-(5-Trifluoromethylpyridin-2-yl)azetidin-3-ylamine. (D7)

D6 (750 mg, 1.28 mM) in dichloromethane (5 ml) was treated with trifluoroacetic acid (5 ml) overnight at ambient temperature. The solution was concentrated and then partitioned between dichloromethane and 2M sodium hydroxide.

The dichloromethane solution was washed with brine, dried and concentrated to give the title compound as a colourless solid, (477 mg).

The following were prepared using a method similar to that employed in Descriptions 6 and 7.

1-(3-Trifluoromethylpyridin-2-yl)azetidin-3-ylamine (D8).

1-(4-Trifluoromethylpyridin-2-yl)azetidin-3-ylamine (D9).

1-(6-Trifluoromethylpyridin-2-yl)azetidin-3-ylamine (D10).

Description 11

[1-(6-Methyl-4-trifluoromethylpyridin-2-yl)azetidin-3-yl] carbamic acid t-butyl ester (D11)

A mixture of (R)-(+)-2,2'-bis(diphenylphosphino)-1,1'-binaphthyl, (BINAP, 382 mg), palladium acetate, (92 mg) and caesium carbonate, (3.36 g, 10.23 mmol) in dry dioxan (20 ml) was sonicated for 50-60 min to give a pink colour. A solution of 3-t-butoxy-carbonylaminoazetidine acetate (ex. WO 98/57640), (950 mg, 4.09 mmol) and 2-chloro-6-methyl-4-trifluoromethylpyridine, (800 mg, 4.09 mmol) in dry dioxan (20 ml) was added. The reaction mixture was degassed, flushed with argon and heated to 100° C. overnight. After work-up with EtOAc and water, the organic layer was washed with brine, dried (MgSO$_4$ and activated charcoal) and concentrated. The crude product was purified by column chromatography to give the title compound as a pale yellow solid, (728 mg, 54%).

Description 12

1-(6-Methyl-4-trifluoromethylpyridin-2-yl)azetidin-3-ylamine (D12)

D11, (728 mg, 2.20 mmol) in DCM (5 ml) was treated with TFA (5 ml) at room temperature for 18 h. The solution was concentrated and partitioned between DCM and 2M NaOH. The organic phase was washed with brine, dried (MgSO$_4$) and concentrated in vacuo to give the title compound as a pale yellow crystalline solid (478 mg, 94%).

Description 13

[1-(6-Chloro-5-trifluoromethylpyridin-2-yl)azetidin-3-yl] carbamic acid t-butyl ester (D13)

3-Butoxycarbonylaminoazetidine acetate (synthesis described in WO 98/57640) (2 g, 8.61 mmol), 2,6-dichloro-5-trifluoromethylpyridine, (2.05 g, 9.47 mmol) and potassium carbonate, (2.5 g, 18.08 mmol) in dry DMF (20 ml) were heated to 100° C. for 16 h. The 2 isomers were separated by column chromatography. [1-(6-chloro-3-trifluoromethylpyridin-2-yl)azetidin-3-yl]carbamic acid t-butyl ester was isolated as a colourless solid, (560 mg, 18%). The title compound, [1-(6-chloro-5-trifluoromethylpyridin-2-yl)azetidin-3-yl]carbamic acid t-butyl ester, was also isolated as a colourless solid (1.92 g, 63%).

Description 14

[1-(6-Methyl-5-trifluoromethylpyridin-2-yl)azetidin-3-yl] carbamic acid t-butyl ester (D14)

A mixture of D13 (1.92 g, 5.55 mmol), methylboronic acid, (490 mg, 8.19 mmol) and tetrakis(triphenylphosphine) Pd(0), (315 mg) in dioxan (25 ml) was treated with aqueous sodium carbonate (7 ml). The mixture was heated at reflux for 16 h, allowed to cool, then diluted with water and extracted with DCM (2×50 ml). The organic phase was washed with brine, dried and concentrated to give a solid. T.I.c anlaysis showed that substantial quantities of starting material remained. The crude material was treated again with methylboronic acid, (490 mg, 8.19 mM) and tetrakis(triphenylphosphine) Pd(0), (315 mg) as above. T.I.c. showed complete conversion to the product which was purified by column chromatography to give the title compound as a colourless solid (1.34 g, 74%).

Description 15

1-(6-Methyl-5-trifluoromethylpyridin-2-yl)azetidin-3-ylamine (D15)

D14 (1.34 g, 4.04 mmol) was deprotected in a similar manner to that described in D12 and gave the title compound as a pale yellow oil (849 mg, 91%).

Description 16

3-Amino-1-diphenylmethylazetidine (D16)

3-Amino-1-diphenylmethylazetidine was prepared according to the procedure in *J. Heterocyclic. Chem.,* 1985, 22, 961.

Description 17

3-Amino-1-di-(4-fluorophenyl)methylazetidine (D17)

The title compound was prepared using a method similar to the procedure in *J. Heterocyclic. Chem.,* 1985, 22, 961.

EXAMPLE 1

N-(2-Bromophenyl)-N'-[(1-(5-trifluoromethyl-2-pyridyl)azetidin-3-yl)]urea (E1)

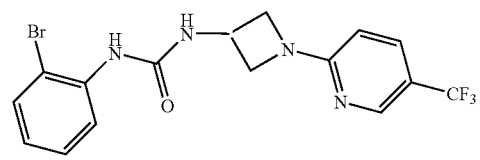

D7 (100 mg, 0.46 mmol) in dichloromethane (2 ml) at ambient temperature was treated with 2-bromophenyl isocyanate (91 mg, 0.46 mmol) in dichloromethane (1 ml). The reaction mixture was maintained at ambient temperature overnight. The white solid was removed by centrifugation and washed with diethyl ether, and dried in vacuo, to give the title compound, (160 mg). MH$^+$ 415, 417.

EXAMPLE 2

N-(3-Methylisoquinolin-5-yl)-N'-[(1-(5-trifluoromethyl-2-pyridyl)azetidin-3-yl)]urea (E2)

D4 (73 mg, 0.46 mmol) in dry dichloromethane (5 ml) was treated with pyridine (45 ul, 0.55 mmol) and phenyl chloroformate (69 ul, 0.55 mmol). After 1 h triethylamine (128 ul, 0.92 mmol) was added, followed by D7 (100 mg, 0.46 mmol). The reaction mixture was then stirred overnight at ambient temperature. The precipitate was separated by centrifugation, washed with dichloromethane then diethyl ether and then dried to give the title compound as a yellow solid (129 mg). MH$^+$ 402.

EXAMPLES 3-35

Examples presented in Table 1 were prepared in accordance with the procedures described herein and similar to those of E1 and E2.

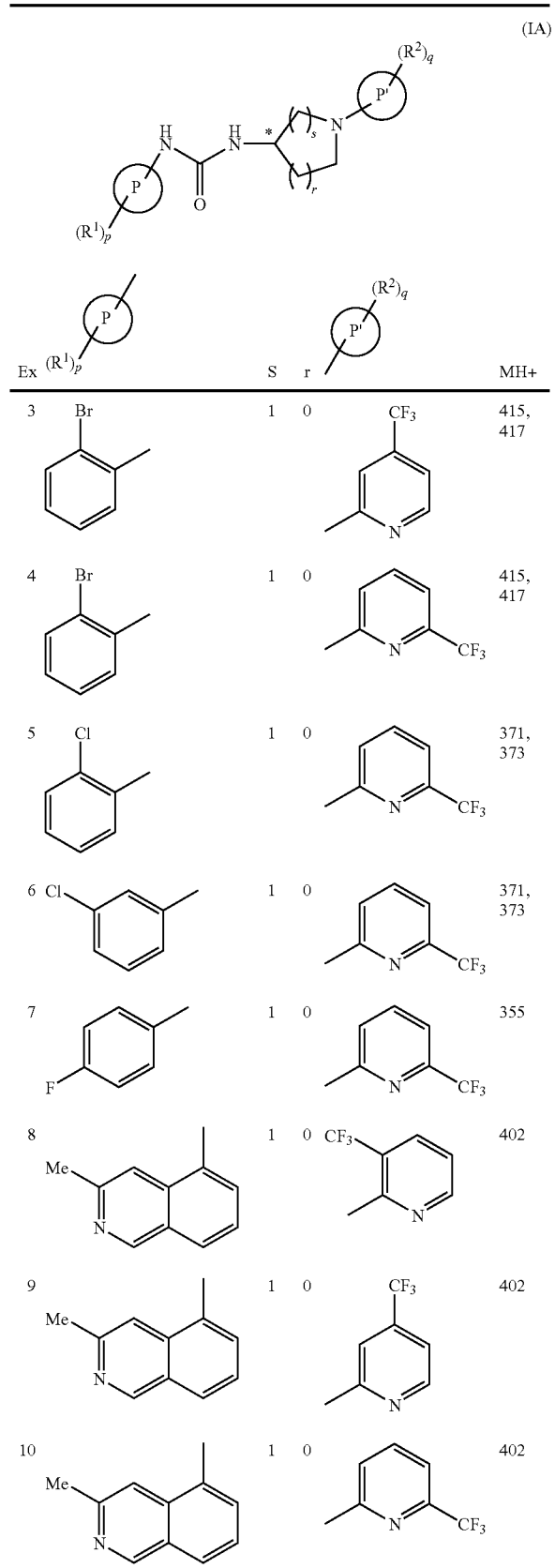
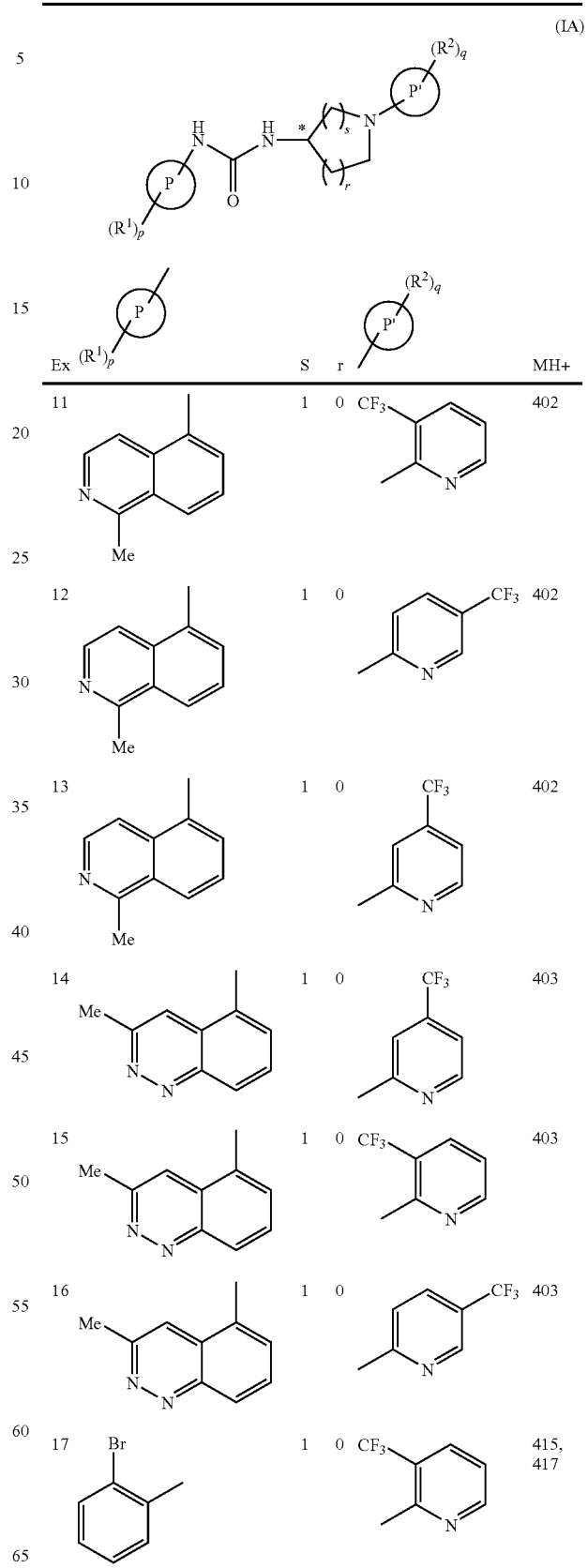

TABLE 1-continued (IA)

| Ex | P (R¹)ₚ | S | r | P' (R²)q | MH+ |
|---|---|---|---|---|---|
| 18 | 2-Cl phenyl | 1 | 0 | 3-CF₃, 2-Me pyridine | 371, 373 |
| 19 | 2-Cl phenyl | 1 | 0 | 4-CF₃, 2-Me pyridine | 371, 373 |
| 20 | 2-Cl phenyl | 1 | 0 | 5-CF₃, 2-Me pyridine | 371, 373 |
| 21 | 3-Cl phenyl | 1 | 0 | 5-CF₃, 2-Me pyridine | 371, 373 |
| 22 | 2,3-diCl phenyl | 1 | 0 | 2-Me, 6-CF₃ pyridine | 405, 407 |
| 23 | 2,5-diCl phenyl | 1 | 0 | 2-Me, 6-CF₃ pyridine | 405, 407 |
| 24 | 2-Cl, 6-Me phenyl | 1 | 0 | 2-Me, 6-CF₃ pyridine | 385, 387 |
| 25 | 2-CF₃ phenyl | 1 | 0 | 2-Me, 6-CF₃ pyridine | 405 |
| 26 | 3-CF₃ phenyl | 1 | 0 | 2-Me, 6-CF₃ pyridine | 405 |
| 27 | 2-Br phenyl | 1 | 0 | 3-CF₃, 2-Me, 6-Me pyridine | 431, 429 |
| 28 | 1-Me, 5-Me isoquinoline | 1 | 0 | 4-CF₃, 2-Me, 6-Me pyridine | 416 |
| 29 | 1-Me, 5-Me isoquinoline | 1 | 0 | 3-CF₃, 2-Me, 6-Me pyridine | 416 |
| 30 | 1-Me, 5-Me isoquinoline | 1 | 0 | 2-Me, 6-CF₃ pyridine | 402 |
| 31 | 2,3-diCl phenyl | 1 | 0 | 3-CF₃, 2-Me, 6-Me pyridine | 419, 421 |

TABLE 1-continued

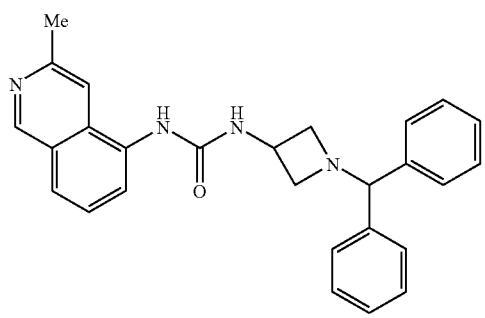

| Ex | (R¹)ₚ | S | r | (R²)q P' | MH+ |
|---|---|---|---|---|---|
| 32 | 2-Cl-phenyl | 1 | 0 | 6-methyl-3-CF₃-2-methyl-pyridin | 383, 385 |
| 33 | 2,3-diCl-phenyl | 1 | 0 | 6-methyl-4-CF₃-2-methyl-pyridin | 419, 421 |
| 34 | 2-Cl-phenyl | 1 | 0 | 6-methyl-4-CF₃-2-methyl-pyridin | 383, 385 |

EXAMPLE 35

N-(2-Bromophenyl)-N'-[1-(6-methyl-4-trifluoromethylpyridin-2-yl)azetidin-3-yl]urea (E35)

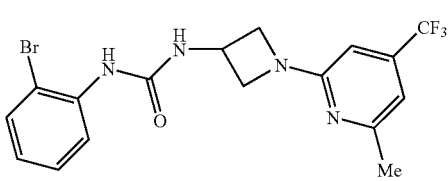

A mixture of 1-(6-methyl-4-trifluoromethylpyridin-2-yl)azetidin-3-ylamine, D12 (100 mg, 0.432 mM) and 2-bromophenyl isocyanate (86 mg, 0.432 mM) in dichloromethane (5 ml) was kept at room temperature overnight. The resultant solid was removed by centrifugation, washed with diethyl ether and dried in vacuo, to give the title compound as a colourless solid, (119 mg, 64%). MH⁺ 429 and 431; ¹H NMR (250 MHz, d⁶DMSO) δ: 2.39 (3H, s), 3.75-3.88 (2H, dd), 4.30 (2H, t), 4.50-4.66 (1H, m), 6.48 (1H, s), 6.78 (1H,s), 6.92 (1H, m), 7.28 (1H, m), 7.57 (1H, dd), 7.76 (1H, d), 7.86 (1H, s), and 8.04 (1H, dd).

EXAMPLE 36

N-(3-Methylisoquinolin-5-yl)-N'(1-diphenylmethylazetidin-3-yl)-urea (E36)

D4 (73 mg, 0.46 mmol) in dry dichloromethane (5 ml) was treated with pyridine (45 ul, 0.55 mmol) followed by phenyl chloroformate (69 ul, 0.55 mmol). After 1 h triethylamine (128 ul, 0.92 mmol) was added, followed by D16 (0.46 mmol). The reaction mixture was then stirred overnight at ambient temperature. The precipitate was separated by centrifugation, washed with DCM, diethyl ether and then dried to give the title compound as a yellow solid. MH⁺ 423.

EXAMPLES 37-41

Examples presented in Table 2 were prepared in accordance with the procedures described herein and similar to those of E36.

TABLE 2

| Ex | (R¹)ₚ P | (R²)q | MH+ |
|---|---|---|---|
| 37 | 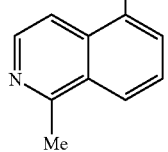 | H | 423 |

TABLE 2-continued (IB)

[Structure showing urea-linked azetidine with diphenylmethyl group, with (R¹)ₚ on ring P and (R²)q on phenyl rings]

| Ex | (R¹)ₚ—P' | (R²)q | MH+ |
|---|---|---|---|
| 38 | 3-methyl-cinnolin-5-yl | H | 424 |
| 39 | 1-methyl-isoquinolin-5-yl | H | 437 |
| 40 | 1-methyl-isoquinolin-5-yl | 4-F | 459 |
| 41 | 2-bromo-methylphenyl | H | 436, 438 |

Pharmacological Data (a) In Vitro Assay

As referenced above, the compounds of the invention are vanilloid receptor VR1) antagonists and hence have useful pharmaceutical properties. Vanilloid receptor (VR1) antagonist activity can be confirmed and demonstrated for any particular compound by use of conventional methods, for example those disclosed in standard reference texts such as D. Le Bars, M. Gozarin and S. W. Cadden, Pharmacological Reviews, 2001, 53(4), 597-652] or such other texts mentioned herein.

The screen used for the compounds of this invention was based upon a FLIPR based calcium assay, similar to that described by Smart et al. (British Journal of Pharmacology, 2000, 129,227-230). Transfected astrocytoma 1321N1 cells, stably expressing human VR1, were seeded into FLIPR plates at 25,000 cells/well (96-plate) and cultured overnight.

The cells were subsequently loaded in medium containing 4 μM Fluo-3 AM (Molecular Probes) for 2 h, at room temperature, in the dark. The plates were then washed 4 times with Tyrode containing 1.5 mM calcium, without probenecid. The cells were pre-incubated with compound or buffer control at room temperature for 30 min. Capsaicin (Sigma) was then added to the cells. Compounds having antagonist activity against the human VR1 were identified by detecting differences in fluorescence when measured after capsaicin addition, compared with no compound buffer controls. Thus, for example, in the buffer control capsaicin addition results in an increase in intracellular calcium resulting in fluorescence. A compound having antagonist activity blocks the capsaicin binding to the receptor, there is no signalling and therefore no increase in intracellular calcium levels and consequently lower fluorescence. pKb values are generated from the $IC_{50}$ values using the Cheng-Prusoff equation.

All compounds tested by the above methodology (Examples 1-41) had pKb>6, preferred compounds (Examples 1-5,8-13, 16, 20, 22-24, 27-29 and 31-40) having a pKb>7.0.

(b) FCA-Induced Hyperalgesia in the Guinea Pig 100 ul of 1 mg/ml FCA was injected intraplantar into the left paw of 4 groups of 8 male Dunkin Hartley guinea-pigs (batch: 6282434, average weight 340 g). 24 hours later compounds were administered orally at 0 (vehicle), 3, 10 30 mg/kg with vehicle as 1% methylcellulose and dosing volume being 2 ml/kg and dosing straight into the stomach. The methylcellulose was added gradually to the compound into the pestle and mortar and ground together.

Behavioural readouts of mechanical hyperalgesia were obtained before FCA administration (naïve reading), after FCA but before drug administration (predose reading) and 1 hour after drug administration. The readout used was paw pressure (Randall-Sellito) and the end point was paw withdrawal. The paw pressure equipment also had one silver disc placed on the point to increase the markings by a factor of 2.

Compounds having a pKb>7.0 in vitro, according to model (a) above, were tested in this model and shown to be active.

The invention claimed is:

1. A compound represented by the following formula:

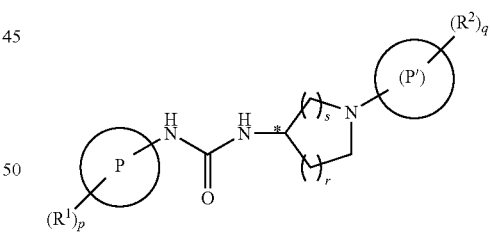

or a pharmaceutically acceptable salt thereof wherein:
P is selected from the group consisting of phenyl, 5-isoquinolinyl, and 5-cinnolinyl; P' is 2-pyridyl;
R¹ and R² are independently selected from the group consisting of halo, —C₁-C₆-alkyl, and —CF₃;
p and q are each independently 0, 1, or 2;
r=0; and
s=1.

2. A compound according to claim 1 or a pharmaceutically acceptable salt thereof wherein P represents phenyl.

3. A compound according to claim 1 or a pharmaceutically acceptable salt thereof wherein p and q each independently represent 1 or 2.

4. A compound according to claim 3 or a pharmaceutically acceptable salt thereof wherein each $R^2$ independently represents —$CH_3$ or —$CF_3$; and each $R^1$ independently —F, —Cl, —Br, $CH_3$, or —$CF_3$.

5. A compound according to claim 1 or a pharmaceutically acceptable salt thereof, which compound is selected from the group consisting of:

N-(2-Trifluoromethylphenyl)-N'-[(1-(6-trifluoromethyl-2-pyridyl)azetidin-3-yl)]urea;

N-(2-Bromophenyl)-N'-[(1-(6-methyl-4-trifluoromethyl-2-pyridyl)azetidin-3-yl)]urea;

N-(2-Chlorophenyl)-N'-[(1-(6-methyl-4-trifluoromethyl-2-pyridyl)azetidin-3-yl)]urea; and N-(2,3-Dichlorophenyl)-N'-[(1-(6-methyl-4-trifluoromethyl-2-pyridyl)azetidin-3-yl)]urea.

6. A pharmaceutical composition comprising a compound according to claim 1 or a pharmaceutically acceptable salt thereof and a pharmaceutically acceptable carrier or excipient.

7. The compound according to claim 1 or a pharmaceutically acceptable salt thereof, wherein P represents 5-isoquinolinyl.

8. The compound according to claim 1 or a pharmaceutically acceptable salt thereof, wherein P represents 5-cinnolinyl.

9. The compound according to claim 6 or a pharmaceutically acceptable salt thereof, where $R^2$ represents $CF_3$.

10. A compound represented by the following formula:

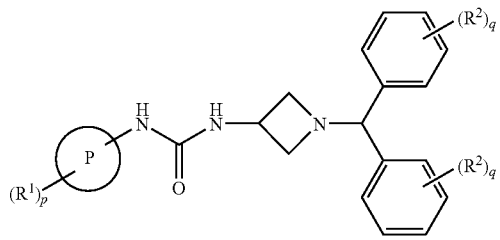

or a pharmaceutically acceptable salt thereof, wherein:
P is selected from the group consisting of phenyl, 5-isoquinolinyl, and 5-cinnolinyl;
each $R^1$ and each $R^2$ are independently selected from the group consisting of halo, —$C_1$-$C_6$-alkyl, and —$CF_3$;
p is 0, 1, or 2; and
each q is independently 0, 1, or 2.

11. The compound of claim 10 or a pharmaceutically acceptable salt thereof wherein each q is 0 or 1; and
each $R^1$ and each $R^2$ are independently —F, —Cl, —Br, —$CH_3$, or —$CF_3$.

12. The compound of claim 11 or a pharmaceutically acceptable salt thereof wherein each q is 1 and each $R^2$ is —F.

13. The compound of claim 11 or a pharmaceutically acceptable salt thereof wherein each q is 0.

14. The compound of claim 10 which is N-(1-Methylisoquinolin-5-yl)-N'-(1-diphenylmethylazetidin-3-yl)-urea or a pharmaceutically acceptable salt thereof.

* * * * *